United States Patent
Isaac et al.

(10) Patent No.: US 6,937,894 B1
(45) Date of Patent: *Aug. 30, 2005

(54) METHOD OF RECHARGING BATTERY FOR AN IMPLANTABLE MEDICAL DEVICE

(75) Inventors: George I. Isaac, Port Hueneme, CA (US); Jorge N. Amely-Velez, Simi Valley, CA (US); Gabriel A. Mouchawar, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 629 days.

This patent is subject to a terminal disclaimer.

(21) Appl. No.: 10/045,844

(22) Filed: Nov. 8, 2001

(51) Int. Cl.[7] ............................................. A61N 1/378
(52) U.S. Cl. ................. 607/5; 607/9; 607/34
(58) Field of Search ............... 607/4–5, 9, 34; 320/103

(56) References Cited

U.S. PATENT DOCUMENTS

| | | | |
|---|---|---|---|
| 5,411,537 A * | 5/1995 | Munshi et al. ................. | 607/33 |
| 5,466,254 A | 11/1995 | Helland ....................... | 607/123 |
| 5,674,248 A * | 10/1997 | Kroll et al. .................... | 607/5 |
| 5,741,307 A * | 4/1998 | Kroll ............................ | 607/5 |
| 6,044,295 A | 3/2000 | Pilz et al. ...................... | 607/4 |
| 6,549,807 B1 * | 4/2003 | Kroll ........................... | 607/34 |
| 6,650,942 B2 * | 11/2003 | Howard et al. ............... | 607/34 |

* cited by examiner

Primary Examiner—Kennedy Schaetzle
Assistant Examiner—Kristen Mullen

(57) ABSTRACT

A method of operating an implantable medical device containing a Lithium Silver Vanadium Oxide battery. In response to a detected need for therapy, a current flow is delivered from the battery to a charge storage device. After the battery is at least partly depleted by one or more such deliveries of current or other power consumption, the battery is recharged. The recharging may be initiated in response to a selected time threshold, a selected number of current flow delivery events, a selected voltage level, an excess charge time duration, or other operating characteristics. A limited number of recharging cycles may be provided if the charging is done under controlled conditions with respect to charge current and voltage.

27 Claims, 4 Drawing Sheets

METHOD OF RECHARGING BATTERY FOR AN IMPLANTABLE MEDICAL DEVICE

FIELD OF THE INVENTION

This invention relates to electronic components for implantable medical devices, and more particularly to recharging batteries for implantable cardioverter/defibrillators.

BACKGROUND OF THE INVENTION

Implantable cardioverter defibrillators (ICDs) are implanted in patients susceptible to cardiac tachyarrhythmias including atrial and ventricular tachycardias and atrial and ventricular fibrillation. Such devices typically provide cardioversion or defibrillation by delivering low voltage pacing pulses or high voltage shocks to the patient's heart of up to 800V. The ICD operates by detecting a fast heart rate or tachyarrhythmia, upon which a battery within the device housing is coupled via an inverter to a high voltage capacitor or capacitors to charge the capacitors. When the capacitors reach a desired voltage, charging is stopped. The capacitors are discharged under control of a microprocessor to provide a therapeutic shock to the patient's heart.

While transcutaneous rechargeable battery systems have been contemplated, for example as provided in U.S. Pat. No. 5,991,665 to Wang et al., such a system has never been implemented in an ICD because of the lack of an acceptable rechargeable battery and the recharging system, and the unsuitability of current battery technologies for recharging.

In addition, a battery in an ICD must be capable of high current rates needed to charge the high voltage capacitors in a short time, so that a therapeutic shock may be delivered within a short time interval after the device has detected and diagnosed a need for the shock. If the battery has an excessive internal resistance, the current flow rate will be limited, delaying capacitor charging. This may result in syncope, ischemia (oxygen starvation) of critical organs and tissues. As a general principle, the sooner the therapy can be delivered following a detected episode, the better prospects are there for the patient's health. In addition, it is believed that therapy delivered more promptly requires a lower energy therapy, allowing the conservation of the battery's energy to extend the device life before replacement is required.

Thus, ICD designers have adopted a class of low internal resistance battery chemistries such as Lithium Pentoxide of which Lithium Silver Vanadium Oxide (SVO) is a member, using one or more such cells in selected ICD applications. These provide the required rapid capacitor charging, and are generally effective over a moderately long life. However, over the life of existing devices, as SVO battery voltage diminishes, the time interval between diagnosis of an arrhythmia and completion of capacitor charging increases, so that the effective device life is limited due to the concerns noted above about delayed treatment.

To provide extended battery life, batteries of various chemistries may be recharged. As noted above, transcutaneous recharging has been contemplated for low-energy implanted devices such as pacemakers. However, the SVO batteries preferred for ICD devices for the reasons above are considered as primary cells and thus not rechargeable by the recommendation of their manufacturers. In certain rechargeable batteries, there remains an inherent concern that multiple recharging cycles may generate elongated dendrites as electrode surfaces are replated. These metal dendrites can cause shorting. Shorting in a battery will tend to deplete it rapidly, prevent subsequent recharging, and render the device inoperable. In addition, lithium clustering, which may generate a particle of lithium between an anode and a cathode in response to rapid charging without precaution, is another known risk of attempting to recharge an SVO cell.

SUMMARY OF THE INVENTION

The disclosed embodiment overcomes the limitations of the prior art by providing a method of operating an implantable medical device containing an SVO battery. Aside from the SVO battery, others of the Lithium Pentoxide class, such as, for example, Lithium Manganese Oxide, may also be used. In response to a detected need for therapy, a current flow is delivered from the battery to a charge storage device. After the battery is at least partly depleted by one or more such deliveries of current or other power consumption, the battery is recharged. The recharging may be initiated in response to a selected time threshold, a selected number of current flow delivery events, a selected voltage level, an excess charge time duration, or other operating characteristics. A limited number of recharging cycles may be provided if the charging is done under controlled conditions with respect to charge current and voltage. As a precaution, the recharge function would be limited so as not to exceed about 10% of the total battery capacity.

BRIEF DESCRIPTION OF THE DRAWINGS

Further features and advantages of the present invention may be more readily understood by reference to the following description taken in conjunction with the accompanying drawings, in which.

DETAILED DESCRIPTION OF A PREFERRED EMBODIMENT

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
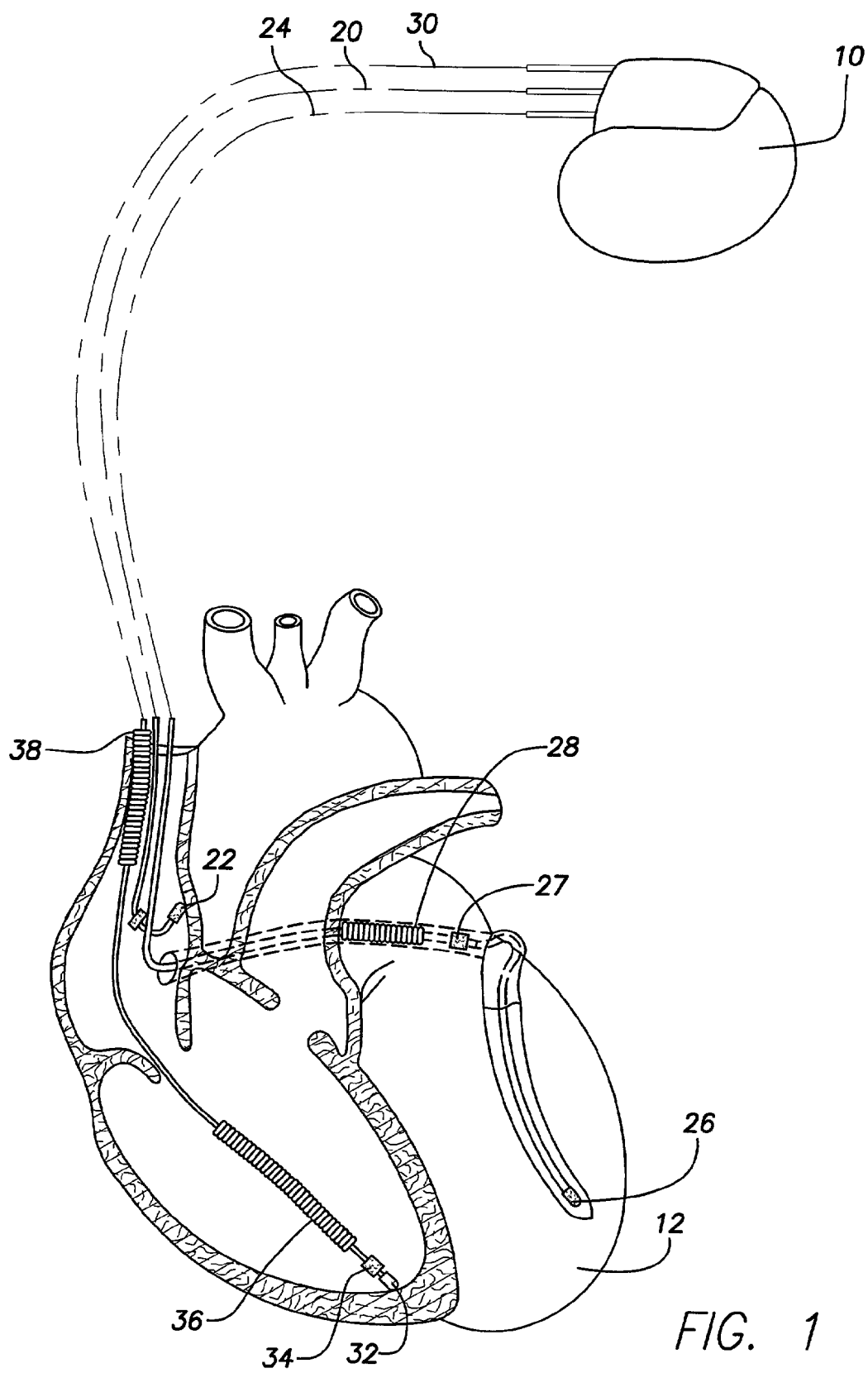
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, "A Self-Anchoring, Steerable Coronary Sinus Lead" (Pianca et al.), and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
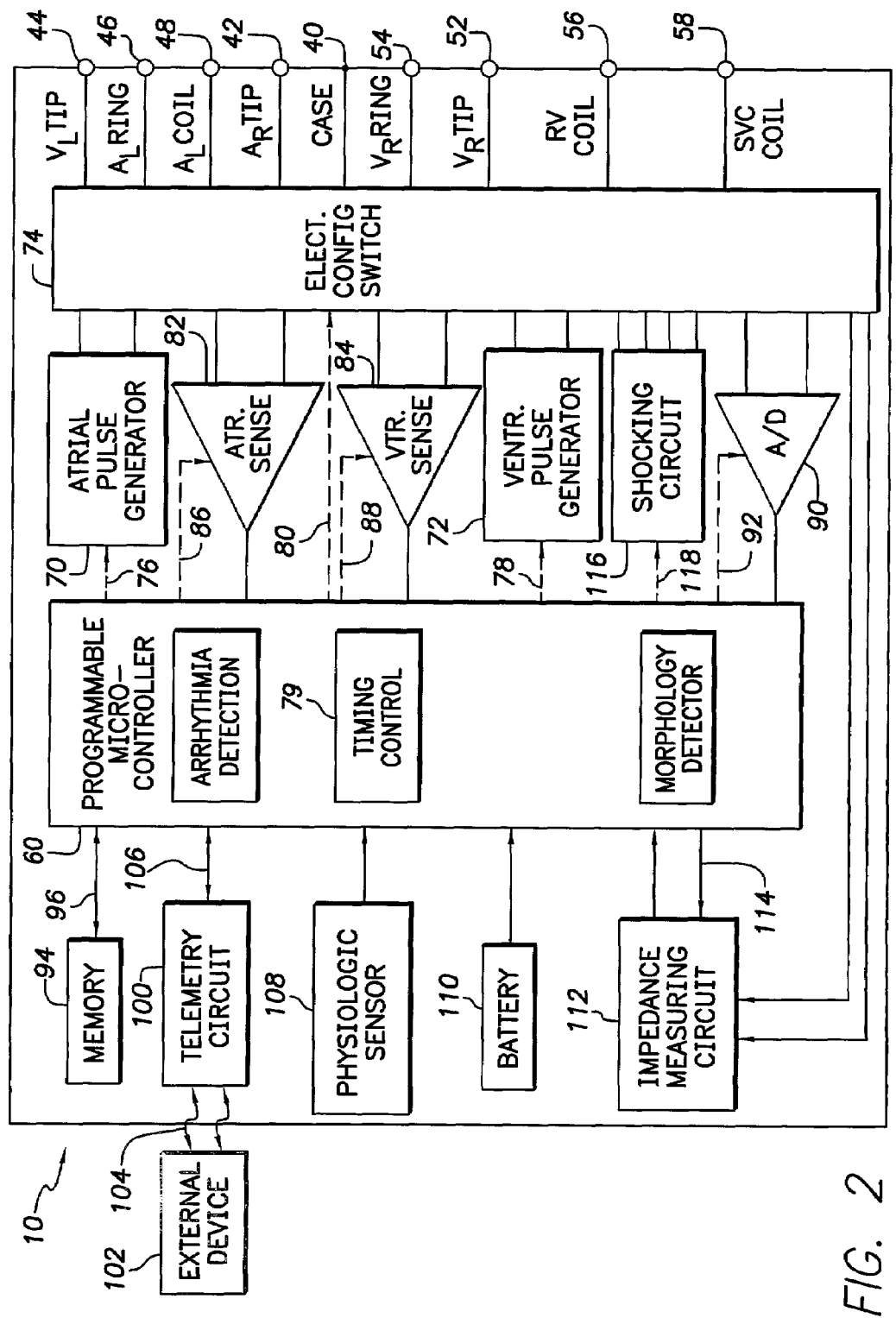
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.)

by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time (preferably less than 10 $\mu$A), and then be capable of providing high-current pulses (for capacitor charging) when the patient requires a shock pulse (preferably, in excess of 2 A, at voltages above 2 V, for periods of 10 seconds or more). The battery 110 must also have a predictable discharge characteristic so that elective replacement time can be detected. Accordingly, the device 10 preferably employs lithium/silver vanadium oxide batteries, as is true for most (if not all) current devices.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11–40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asychronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
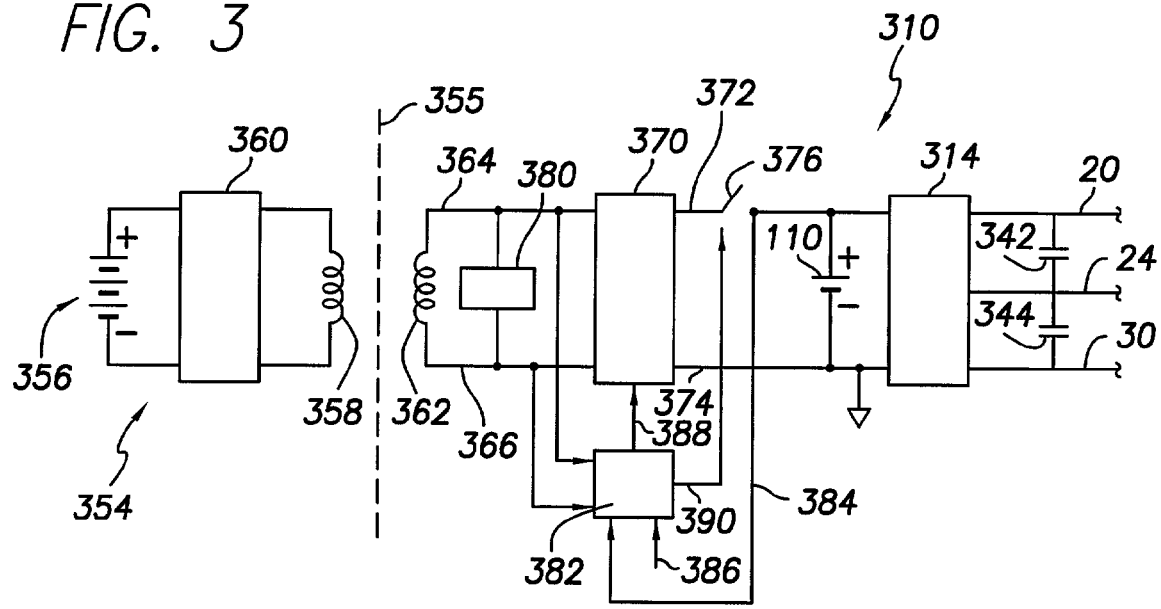
FIG. 3 is a schematic block diagram of implantable defibrillator circuitry according to a preferred embodiment of the invention.

FIG. 3 illustrates cardioverter/defibrillator (ICD) circuitry 310 adapted for use in conjunction with and as part of the device discussed above with respect to FIGS. 1 and 2. The circuitry includes a battery 110 with both electrodes connected to conventional defibrillator output circuitry 314, all contained in a metallic conductive housing. The battery 110 may be any of a number of batteries selected from the class of Lithium Pentoxide batteries, and in the preferred embodiment, is a Lithium Silver Vanadium Oxide (SVO) battery cell.

The circuitry 314 is a high voltage DC-to-DC converter that includes switching circuitry and a controller and power supply circuit, as discussed above with respect to FIGS. 1 and 2. The circuitry 314, which is controlled by the microcontroller 60 includes a DC-to-DC voltage converter (not shown), which is connected to a pair of high voltage capacitors 342, 344. Switch 74 is connected to the converter 314 and ground, so that a pulsing current may be used to generate a high voltage to charge the capacitors 342 and 344.

In the preferred embodiment, a battery having a voltage of about 3V, can result in a potential of up to about 800V to be developed across the capacitors 342 and 344.

The ICD circuitry 310 controls the periodic recharging of the SVO cell 110 from an external recharger 354 located externally of the patient, whose skin barrier is represented by dotted line 355. The recharger may be a hand-held unit including a battery 356 and a transmitter coil 358 connected via a DC-to-AC converter 360 that includes conventional circuitry including oscillators and switching control logic circuitry known in the art.

The ICD circuitry 310 includes a receiver coil 362 configured for transcutaneous inductive or other coupling with the transmitter for recharging. The receiver coil 362 has two leads 364, 366 connected to two inputs of a rectifier 370. The rectifier 370 has two output lines 372, 374 with output line 372 connected via a switch 376 to the anode of the SVO battery 110. The rectifier 370 operates to convert the alternating input current from the receiver coil 362 to a DC current suitable for charging the battery 110 when the switch 376 is closed.

An Over-Voltage Protection (OVP) circuit 380 is connected between leads 364 and 366, and limits undesirable high voltages induced in the receiver coil 362 from reaching the rectifier 370 and the converter 314. On occasions, a patient may be unexpectedly exposed to unusually high energy magnetic or electric fields generated by certain machinery or apparatus, and the OVP circuitry 380 protects the device and patient from the adverse effects of unwanted high energy fields. A charge controller 382 has input lines connected to the leads 364, 366, a battery voltage monitor input line 384 connected to the anode of the SVO battery 110, a reference voltage input line 386, and a rectifier controller line 388 coupled to the rectifier 370. A switch control line 390 extends to the switch 376 for selectively opening and closing the switch.

The controller 382 operates to maintain the charging switch 376 in a normally open position, except when charging is desired. The charge controller 382 operates so as to maintain the switch 376 open when the receiver voltage is below the battery voltage, to prevent the SVO battery 110 from being drained into the recharging circuitry.

Furthermore, the switch is maintained open when the SVO battery voltage exceeds a reference voltage applied at reference voltage node 386. This serves to terminate recharging operations when the SVO battery 110 is charged to the reference value typically indicating that the SVO battery is fully charged. This also serves to prevent initiation of recharging when the SVO battery 110 remains fully charged. In practice, the sensed and compared voltages need not be the actual voltages provided by direct lines as illustrated for clarity. In the preferred practice, the reference voltage may be a logic level voltage below the SVO battery voltage, requiring the battery voltage to be stepped down by a resistor divider or other means.

The rectifier 370 is essentially an AC-to-DC converter, and is preferably a synchronous rectifier that provides more efficient conversion than a passive rectifier using a diode bridge, thereby reducing the voltage drop across diodes and reducing heat dissipated, and speeding recharging time. The charge controller 382 operates to sense the phase of the voltage of the receiver coil 362, and to control timing or the rectifier function via control line 388.

Figure 4:
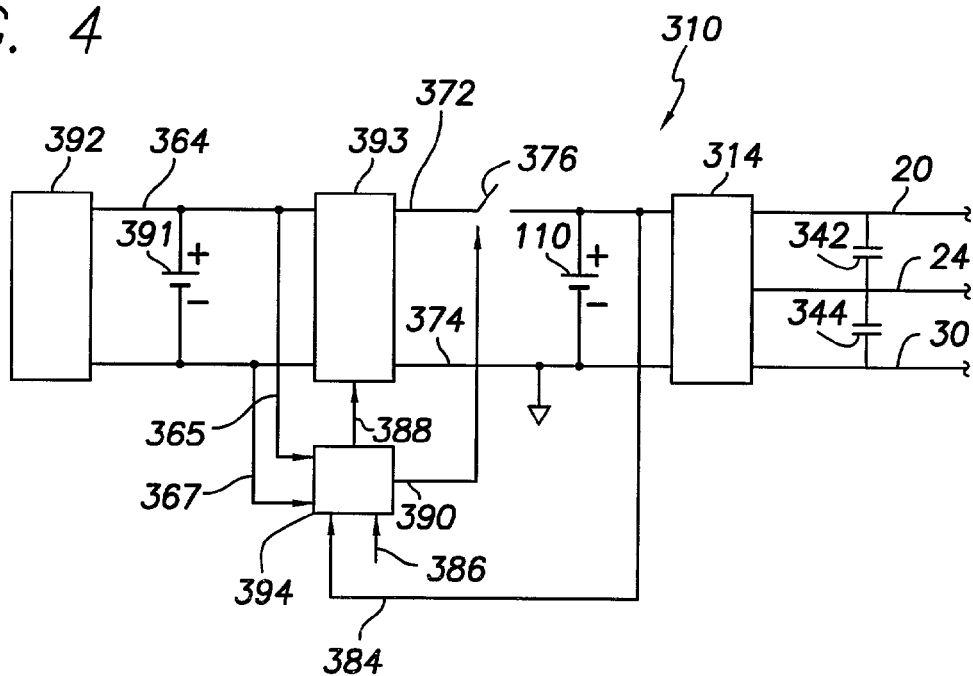
FIG. 4 is a schematic block diagram of an implantable defibrillator circuitry according to an alternative embodiment of the invention.

FIG. 4 shows an alternative embodiment cardioverter/defibrillator (ICD) circuitry 310' in which recharging of the SVO battery 110 is accomplished by the use of a second battery 391 internal to the ICD. The second battery 391 has a higher stored energy density, such as provided by a Lithium Carbon Monofluoride (CFx) cell. The circuitry 310' has low voltage pacing and sensing circuitry 392 that is directly connected to and powered by the second battery 391. The ongoing low-voltage functions are preferably provided in this direct fashion, as opposed to the less desirable alternative of being powered by the SVO battery 110, which would entail conversion/charging inefficiencies that are preferably avoided.

A voltage conditioner 393 has two inputs connected to the electrodes of the second cell 391. The conditioner 393 is a DC-to-DC converter that functions to maintain voltage and current balance between the CFx cell 391 and the SVO battery 110 to a level suitable for charging the SVO battery 110. The conditioner 393 may include adaptive control circuitry that actively determines the optimal conversion mode, to reduce conversion losses.

An analog/digital controller 394 has two inputs, i.e., lines 365 and 367, monitoring the voltage of the CFx cell 391, an input connected to the SVO cell anode via line 384, and a reference voltage input 386. A conditioner control line 388 connects to the conditioner 393, and a switch control line 390 connects to the switch 376. The controller operates as in the embodiment of FIG. 3 to prevent overcharging, and to prevent discharging of the SVO battery 110 into the conditioner circuitry.

The battery 110 is preferably a Lithium Silver Vanadium Oxide cell such as are available from Wilson Greatbatch, Ltd. of Clarence, N.Y. with a volume of less than 3 cc, and an open circuit voltage of 3.2V at its "beginning-of-life" (or discharge). The loaded battery voltage ranges between 3.0 and 1.7 volts during the course of battery life, depending on current drain. The loaded voltage is the battery voltage when the battery is connected to the low resistance load of the converter 393. The battery 110 has a theoretical capacity range of 0.3–0.7 Amp-hrs and an internal resistance of 0.3–3.0 ohms. In the preferred embodiment, the resistance of the SVO battery naturally changes tolerably over the device life, beginning at 0.8 ohms, reducing to 0.5 ohms in the middle of life, and increasing above 1.0 ohm at the end-of-life.

Alternative battery chemistries include Lithium Ion with a Cobalt-based cathode, or any comparable chemistry existing or yet to be developed with the general characteristics and qualities of very low internal resistance yielding a high current carrying capability, and a low self discharge rate.

In the preferred embodiment, the battery 110 has a lithium anode. Historically, Lithium Silver Vanadium Oxide cells have been used in implantable defibrillators due to their high current carrying capability. However, recharging cells with lithium anodes has previously been avoided in many applications, for the following reasons. SVO cells have normally been considered as primary cells which are not rechargeable, or which, if recharged, will not perform as expected. Thus, the recharging of lithium anode cells has been avoided for use in implantable medical devices. However, the preferred embodiment avoids the risk of overcharging by limiting recharge rate and voltage, in order to achieve the unexpected results explained below.

An SVO cell that is recharged stores energy as a result of the transfer of lithium anions (Li+) from the cathode to the anode, thereby increasing the voltage of the cell. When energy is drawn from the battery, the Lithium material is de-plated (transferred) from the anode back to the cathode, and stored energy is released. A typical SVO cell provides only a narrow spacing between electrodes, which are separated by a polypropylene separator layer.

Operation of the invention proceeds by recharging the battery periodically. The selection of when to recharge is important, and affects overall battery life. It is desirable to prolong the life of the implanted device and/or to maximize the total number of shocks available to be delivered for patient therapy, since this is the best measure of the useful life of the device. After the end of the life of the device, the device must be surgically replaced. The end of a device's life occurs when the time required for the battery to charge the capacitors in preparation for delivery of therapy shocks exceeds a predetermined threshold, such as about 20 seconds. Beyond this threshold, the delay for delivering therapy is considered to be medically unacceptable, and testing has shown that beyond such a threshold, the remaining battery energy is minimal, even if a few more delayed-response shocks were considered tolerable.

The end-of-life charge time is not merely a matter of a time threshold, but a reflection of observed performance characteristics. It has been found that the charge time duration remains relatively flat, within a few seconds over a battery's life (measured in number of shocks delivered), gradually increasing until nearly the end-of-life, and then rapidly increasing at a much greater rate. During this end-of-life mode, the charge time increases significantly than for the prior charging cycle. Therefore, some systems may have charge time thresholds that greatly differ from the 20-second example noted above. However, such systems will still exhibit significantly increasing charge times that indicate end of battery life.

It has been found that recharging an SVO cell after it has reached its end-of-life as described above will extend the useful battery life significantly. In one experiment, a new SVO cell at the beginning-of-life had an open cell (free) voltage of 3.26 V. This cell underwent an accelerated discharge consisting of five consecutive 800 V charges per hour (for a number of hours (simulating five therapy deliveries each hour). This is equivalent to a drain of 40 mAh of charge drained per hour. The cell demonstrated that it can deliver up to 153 charges before reaching an end-of life open cell voltage of 2.35 V.

After this discharge cycle, the battery was recharged using a current limit of 100 mA until the open cell voltage was 3.2 V. This recharging process required about 8 hours. The recharged battery was then discharged in the same manner as during the first phase. During this second phase, the battery delivered 121 charges before its voltage dropped below the minimum threshold voltage of 2.35 V. After the $125^{th}$ charge of the second phase, the cell was unable to fully charge the capacitors to 800 V within the time threshold of 30 seconds.

The twice-discharged cell was then recharged again in the same manner as above, until the cell reached a free voltage of 3.26 V, after which the cell was again subjected to the cycle of discharges. On the third phase, the cell delivered 30 charges before reaching the charge-time threshold of 30 seconds. Based on this initial experiment, it was concluded that important chemical reactions in the SVO cell are reversible for at least 1 additional phase following total discharge, approximately doubling battery life.

Figure 5:
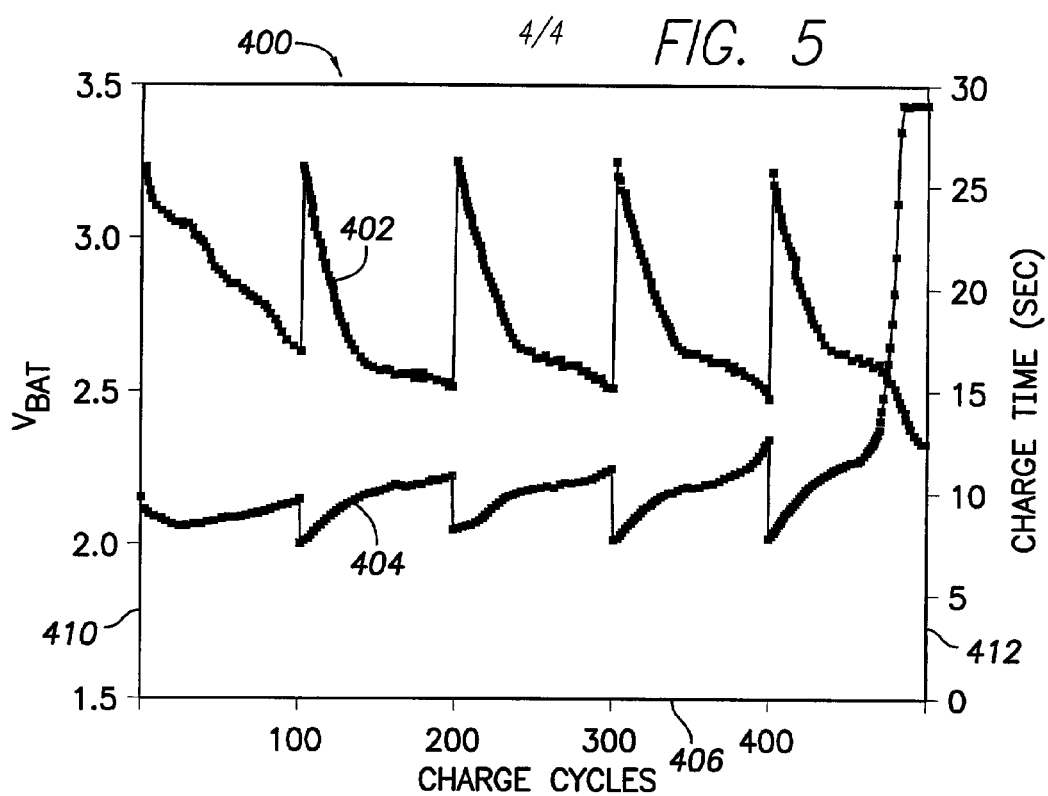
FIG. 5 is a graph illustrating operating performance of the preferred embodiment of the invention under a first set of operating parameters.

It has been determined that battery life can be significantly extended by a recharging process that is initiated well before the end of the battery life. FIG. 5 shows a graph 400 illustrating the results of a second experiment. A first curve 402 indicates the battery's free voltage as measured prior to each charge cycle. A second curve 404 indicates the time for the battery to charge the capacitors to the voltage noted above. The X-axis 406 indicates the number of charge cycles in which the battery rapidly charges the capacitors for delivery of a therapeutic shock (not to be confused with a battery recharge cycle, only several of which are indicated on the graph.) The left Y-axis 410 indicates the battery's free voltage, and the right Y-axis 412 indicates the capacitor charge time in seconds.

The experiment as shown in FIG. 5 proceeds by subjecting the battery to 100 capacitor-charging cycles (one per hour) before each recharge operation. The selection of 100 cycles is intended to be well before the expected end-of-life of the battery (153 cycles in the initial experiment above.) Curve 402 shows how the battery voltage decreases during each charge phase. After each recharge, the battery voltage returns to its initial voltage value. The first cycle demonstrates a relatively smooth downward slope, with the voltage being at or above 2.6 V upon reaching the $100^{th}$ cycle. Subsequent recharge cycles demonstrate a more rapid slope during the first 25–30 charge cycles of each recharge phase, with the voltage flattening out to a gentler slope at about 2.5 V. On the $5^{th}$ recharge phase, the voltage drops below 2.5 V after about 75 cycles, and continues downward to levels considered below tolerable limits.

The charge time curve 404 of FIG. 5 shows relatively stable charge times in the first phases, with gentle increases between recharges. Throughout, charge times remain well below 15 seconds. On the $5^{th}$ phase, at about the $75^{th}$ cycle, the charge time exceeds 15 seconds, and reaches above 30 seconds at about the $80^{th}$ charge of the phase. This demonstrates a useful life of about 475 cycles, as compared to the useful life of less then 200 cycles demonstrated in the initial experiment above. By initiating recharging after a limited number of cycles, the battery voltage is never permitted to drop below a level much below 2.5 V. Similarly, the charge time never exceeds 15 seconds.

Figure 6:
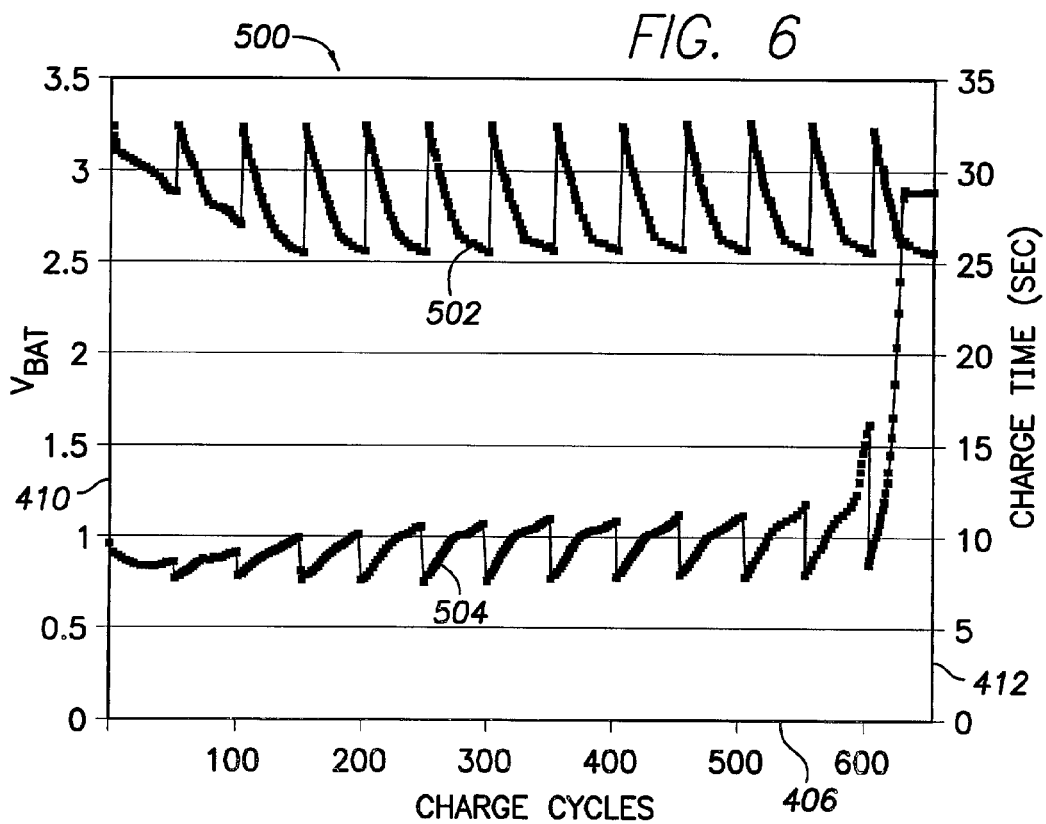
FIG. 6 is a graph illustrating operating performance of the preferred embodiment of the invention under a second set of operating parameters.

A third experiment is illustrated by graph 500 of FIG. 6, which shows an experiment similar to those above, except in which each recharge phase is limited to only 50 capacitor charge cycles (one per hour.) As illustrated, the voltage curve 502 remains above 2.5 V throughout the experiment, and the charge time remains below 15 seconds until nearly the 600$^{th}$ cycle. Even after the 600$^{th}$ cycle, assuming that the 16 second charge time is below a selected threshold as an end-of-life indicator, the battery functions adequately for about 25 more cycles, until the recharge time exceeds 30 seconds (indicated by a flat line reflecting that the capacitors never reached the required 800 V level during the maximum 30 seconds allotted during the experiment.)

It is believed that initiating recharging frequently, after a limited number of charge cycles maximizes battery life. Where recharging is very convenient, it may be initiated after each therapy event, or as often practical after each series of events. Normally, a patient will visit the doctor periodically, such as every few months, for the doctor to read out the battery charge level from the ICD. If below a certain level, recharging is initiated. Even if no events occur during an extended period, the battery may be "topped off" with a recharge to restore the voltage to a maximum level to compensate for leakage and power consumed by device monitoring and other circuitry even when shocks are not delivered. If single events occur only rarely, the device may be recharged after each event. If events occur more rapidly, such as in clusters, recharging may be made at moderate time intervals, such as monthly, or longer intervals. In any event, recharging preferably occurs after a limited number of shocks have been delivered, to provide the extended life benefits demonstrated in the example of FIG. 5.

Although the illustrated example initiates recharging after a limited selected threshold number of therapy deliveries, the principle of the invention may be employed by using other events for initiating recharging.

For instance, the control circuitry in the device may detect the battery free voltage level, and trigger a reminder for recharging when the voltage drops below a selected level, or a selected percentage of the initial voltage.

Alternatively, the circuitry could monitor the capacitor charge time, and request or initiate recharging after the charge time exceeds a preselected limits or when the rate of change of the charge time exceeds a preselected level, or when the charge time exceeds the previous charge time by a selected amount.

Also, recharging may be triggered after a determination that a limited percentage of the energy storage capacity of the battery has been depleted. In such a system, a percentage of 20–50% is believed to be effective to provide an extended battery life.

After experimentation, the useful life of a battery may be confidently determined, so that it is not necessary to monitor various parameters to determine when the battery is in fact depleted. In such an example, a conservative number of cycles is preselected as the limit of battery life, with an adequate margin of safety to allow for variations between devices and operating conditions.

In actual use for an implanted device, the external recharging process preferably employs a hand-held recharger device external to the patient. The recharger is placed on the patient's skin or clothing adjacent to the site of the implanted ICD device. The ICD device contains a coil and connected rectifying circuitry connected to the SVO battery. Operation of the recharger induces alternating currents in the coil, which inductively couples electrical energy to the device coil, charging the battery. The frequency of the recharger current is selected to avoid interference with frequencies employed by other device circuitry, particularly those employed by sensing circuitry and/or other external equipment. Upon reaching a selected threshold voltage, the device generates a signal indicating that recharging is required. It is believed that the 8-hour charging cycle employed for the above experiment may be shortened in practice, for the convenience and comfort of the patient.

In the case of an internal high density cell recharging an SVO cell as illustrated in FIG. 4, the recharging process will be automatic and transparent to the patient. Based on recharge criteria, device electronics inside the ICD determine when to start the recharging process and when to stop.

While described in terms of a preferred embodiment, the invention need not be so limited.

What is claimed is:

1. A method to deliver stimulation energy to selected cardiac tissue with an implantable cardiac stimulation device, comprising:
   sensing physiological cardiac events;
   disposing a Lithium Pentoxide (LP) battery within the implantable cardiac stimulation device;
   charging storage capacitors with the LP battery, the storage capacitors storing electrical stimulation energy;
   delivering the electrical stimulation energy to selected cardiac tissue upon the sensing of physiological cardiac events;
   disposing a supply battery within the implantable cardiac stimulation device;
   switchably connecting the supply battery in parallel to the LP battery to enable the supply battery to recharge the LP battery when voltage across the LP battery falls below a predetermined minimum value;
   detecting when a recharging current is above a predetermined threshold indicative of abnormal recharging of the LP battery; and
   disabling the supply battery whenever an abnormal recharging current is detected.

2. The method of claim 1 wherein the LP battery is a Lithium Silver Vanadium Oxide (SVO) battery.

3. The method of claim 1 wherein the LP battery has a stored energy density and the supply battery has a stored energy density greater than that of the LP battery.

4. The method of claim 1 wherein the supply battery comprises Lithium Carbon Monofluoride (CFx).

5. A method to deliver stimulation energy to selected cardiac tissue with an implantable cardiac stimulation device, comprising:
   sensing physiological cardiac events;
   disposing a Lithium Pentoxide (LP) battery within the implantable cardiac stimulation device;
   charging a storage capacitor with the LP battery to store electrical stimulation energy, the LP battery charging the storage capacitor in a capacitor charge cycle, the capacitor charge cycle defining a charge cycle time;
   delivering the electrical stimulation energy to selected cardiac tissue upon the sensing of physiological cardiac events;
   disposing a supply battery within the implantable cardiac stimulation device; and
   switchably connecting the supply battery in parallel to the LP battery to enable the supply battery to recharge the LP battery when the charge cycle time exceeds a preselected value.

6. The method of claim 5 wherein the LP battery is a Lithium Silver Vanadium Oxide (SVO) battery.

7. The method of claim 5 wherein the LP battery has a stored energy density and the supply battery has a stored energy density greater than that of the LP battery.

8. The method of claim 5 wherein the supply battery comprises Lithium Carbon Monofluoride (CFx).

9. An implantable cardiac rhythm device comprising:
a sensing circuit configured to sense physiological cardiac events;
a pulse generator configured to deliver electrical stimulation energy to selected cardiac tissue upon the sensing of selected cardiac events, the pulse generator having storage capacitors that store the stimulation energy;
a Lithium Pentoxide (LP) battery coupled to the storage capacitors, the LP battery providing a charging current to charge the storage capacitors to preselected energy level;
a supply battery, switchably connected in parallel to the LP battery, having characteristics that enable the supply battery to recharge the LP battery;
a recharging circuit coupled to the LP battery and configured to deliver recharging current to the LP battery; and
a controller programmed to enable the supply battery to recharge the LP battery when voltage across the LP battery falls below a predetermined minimum value.

10. The device of claim 9, wherein the LP battery is a Lithium Silver Vanadium Oxide (SVO) battery.

11. The device of claim 9, wherein the LP battery is recharged upon the detection of a predetermined number of deliveries of stimulation energy.

12. The device of claim 9, further comprising a LP battery voltage detector, operative to cause the LP battery to be recharged when the LP battery voltage is detected as being below the predetermined minimum value.

13. The device of claim 9, further comprising a charging time interval detector configured to monitor the charging time interval required to charge the storage capacitor to the preselected energy level and operative to cause the LP battery to be recharged when the charging time interval is detected to exceed a preselected value.

14. The device of claim 9, wherein the LP battery has a maximum energy capacity and wherein the LP battery is recharged at a rate less than a predetermined maximum charging rate to prevent LP battery degradation.

15. The device of claim 9, wherein the recharging circuit includes a receiver coil adapted for magnetic coupling to an external transmitter coil, wherein the LP battery is recharged as a function of the energy transmitted by the external transmitter coil.

16. The device of claim 9, wherein the LP battery has a stored energy density and the supply battery has a stored energy density greater than that of the LP battery.

17. The device of claim 16, wherein the supply battery comprises a relatively high energy density battery.

18. The device of claim 16, wherein the supply battery comprises Lithium Carbon Monofluoride (CFx).

19. An implantable cardiac rhythm management device comprising:
a pulse generator adaptively configured to generate electric shocks for delivery to a patient's heart comprising:
at least one output capacitor;
charging circuitry capable of charging the at least one capacitor to produce high voltage shocks for delivery to a patient's heart;
a first battery switchably coupled to the charging circuitry, having the characteristic of a high current flow rate to fast charge the at least one capacitor;
a second battery, switchably connected in parallel to the first battery, having characteristics that enable the second battery to recharge the first battery;
a detector, coupled to the charging circuitry, that detects when the recharging current is above a predetermined threshold indicative of abnormal recharging of the first battery; and
a controller programmed to switchably enable the charging circuitry to produce the high voltage shocks, and to disable the second battery whenever an abnormal recharging current is detected;
wherein the controller is further programmed to enable the second battery to recharge the first battery when the voltage across the first battery falls below a predetermined minimum value.

20. The device of claim 19 wherein the first battery has a battery end of life and the controller is programmed to enable the second battery to recharge the first battery prior to reaching the end of life thereof.

21. The device of claim 19 wherein the first battery charges the at least one capacitor in a capacitor charge cycle and wherein the controller is programmed to recharge the first battery upon the occurrence of a predetermined number of capacitor charge cycles.

22. The device of claim 19 wherein the first battery comprises a Lithium Pentoxide cell.

23. The device of claim 22 wherein the Lithium Pentoxide cell comprises a Lithium Silver Vanadium Oxide (SVO) cell.

24. The device of claim 19 wherein the second battery comprises a Lithium Carbon Monofluoride (CFx) cell.

25. An implantable cardiac rhythm management device comprising:
a pulse generator adaptively configured to generate electric shocks for delivery to a patient's heart comprising:
at least one output capacitor;
charging circuitry capable of charging the at least one capacitor to produce high voltage shocks for delivery to a patient's heart;
a first battery switchably coupled to the charging circuitry, having the characteristic of a high current flow rate to fast charge the at least one capacitor;
a second battery, switchably connected in parallel to the first battery, having characteristics that enable the second battery to recharge the first battery;
a detector, coupled to the charging circuitry, that detects when the recharging current is above a predetermined threshold indicative of abnormal recharging of the first battery; and
a controller programmed to switchably enable the charging circuitry to produce the high voltage shocks, and to disable the second battery whenever an abnormal recharging current is detected;
wherein a capacitor charge cycle defines a charge cycle time, and wherein the controller is programmed to recharge the first battery when the charge cycle time exceeds a preselected value.

26. An implantable cardiac rhythm management device comprising:
a pulse generator adaptively configured to generate electric shocks for delivery to a patient's heart comprising:
at least one output capacitor;
charging circuitry capable of charging the at least one capacitor to produce high voltage shocks for delivery to a patient's heart;

a first battery switchably coupled to the charging circuitry, having the characteristic of a high current flow rate to fast charge the at least one capacitor;

a second battery, switchably connected in parallel to the first battery, having characteristics that enable the second battery to recharge the first battery;

a detector, coupled to the charging circuitry, that detects when the recharging current is above a predetermined threshold indicative of abnormal recharging of the first battery; and a controller programmed to switchably enable the charging circuitry to produce the high voltage shocks, and to disable the second battery whenever an abnormal recharging current is detected;

wherein the controller is programmed to periodically recharge the first battery independent of the number of occurrences of the delivery of high voltage shocks.

27. An implantable cardiac rhythm device comprising:

a sensing circuit configured to sense physiological cardiac events;

a pulse generator configured to deliver electrical stimulation energy to selected cardiac issue upon the sensing of selected cardiac events, the pulse generator having storage capacitors that store the stimulation energy;

a Lithium Pentoxide (LP) battery coupled to the storage capacitors, the LP battery providing a charging current to charge the storage capacitors to preselected energy level;

a supply battery, switchably connected in parallel to the LP battery, having characteristics that enable the supply battery to recharge the LP battery; and a recharging circuit coupled to the LP battery and configured to deliver recharging current to the LP battery;

wherein a capacitor charge cycle defines a charge cycle time, and wherein the recharging circuit recharges the LP battery when a charge cycle time exceeds a preselected value.

* * * * *